United States Patent [19]

Maurer et al.

[11] Patent Number: 5,010,193
[45] Date of Patent: Apr. 23, 1991

[54] PREPARATION OF PHOSPHORIC ACID DERIVATIVES AND INTERMEDIATES

[75] Inventors: Fritz Maurer; Reinhard Lantzsch, both of Wuppertal; Helmut Fiege; Albert Schnatterer, both of Leverkusen, all of Fed. Rep. of Germany

[73] Assignee: Bayer Aktiengesellschaft, Leverkusen, Fed. Rep. of Germany

[21] Appl. No.: 282,712

[22] Filed: Dec. 9, 1988

[30] Foreign Application Priority Data

Dec. 18, 1987 [DE] Fed. Rep. of Germany ....... 3742983
Jun. 14, 1988 [DE] Fed. Rep. of Germany ....... 3820176

[51] Int. Cl.$^5$ ................. C07F 9/6512; C07D 239/36; C07D 239/46
[52] U.S. Cl. ..................................... 544/243; 544/298
[58] Field of Search ................................ 544/243, 298

[56] References Cited

U.S. PATENT DOCUMENTS

| | | | |
|---|---|---|---|
| 2,704,757 | 3/1955 | Dornfeld | 544/298 |
| 2,899,426 | 8/1959 | Bloom | 544/298 X |
| 2,919,274 | 12/1959 | Faust et al. | 544/298 |
| 2,994,695 | 8/1961 | Gallaghan et al. | 544/298 |
| 3,041,338 | 6/1962 | Phillips | 544/298 |
| 4,127,652 | 11/1978 | Maurer et al. | 544/243 X |
| 4,429,125 | 1/1984 | Reifschneider | 544/243 |
| 4,666,894 | 5/1987 | Maurer et al. | 514/86 |
| 4,667,034 | 5/1987 | van de Moesdijk et al. | 544/242 |
| 4,686,290 | 8/1987 | Maurer | 544/243 |
| 4,775,755 | 10/1988 | Teunissen et al. | 544/242 |
| 4,880,929 | 11/1989 | Teunissen et al. | 544/242 |

FOREIGN PATENT DOCUMENTS

| | | | |
|---|---|---|---|
| 0193973 | 9/1986 | European Pat. Off. | 544/242 |
| 0320796 | 6/1989 | European Pat. Off. | 544/243 |
| 3423623 | 1/1986 | Fed. Rep. of Germany | |
| 2365577 | 9/1977 | France | |
| 8603168 | 7/1988 | Netherlands | 544/242 |

OTHER PUBLICATIONS

Faust, et al. (S), Chemical Abstracts, vol. 56: 8714a–8715d (1962).
Faust, et al., J. Am. Chem. Soc., vol. 81, pp. 2214–2219 (05/05/59).

*Primary Examiner*—Diana Rivers
*Attorney, Agent, or Firm*—Sprung Horn Kramer & Woods

[57] ABSTRACT

A process for the preparation of a compound of the formula $$R-\underset{N=}{\overset{N-}{\diagup}}\!\!\diagdown\!\!-O-\overset{Y}{\underset{R^1}{\overset{\|}{P}}}\diagdown OR^2 \quad (I)$$

in which
R is hydrogen, alkoxy, alkylamino, dialkylamino or an optionally substituted radical from the group consisting of alkyl, cycloalkyl, aralkyl and aryl,
$R^1$ is an optionally substituted radical from the group consisting of alkyl, alkoxy, alkylthio, mono- or dialkylamino and phenyl,
$R^2$ is optionally substituted alkyl, and
Y is oxygen or sulphur, comprising
(a1) reacting a compound of the formula $$R-C\diagdown\!\!\overset{NH_2^{\oplus}Cl^{\ominus}}{\underset{R^3}{\diagup}} \quad (IIa)$$

with $$\underset{NH_2-CH_2}{\overset{NH_2-CH_2}{\diagdown}}\!\!CH-OH \quad (III)$$

or with $$R^5\ COOH$$

in which
$R^5$ is R except for hydrogen, or equivalent, to produce $$R-\underset{\underset{H}{|}}{\overset{N-CH_2}{\diagup}}\!\!\diagdown\!\!\underset{N-CH_2}{\overset{H}{\diagup}}\!\!\diagdown\!\!\underset{OH}{\overset{}{\diagup}} \quad (IVa)$$

oxidizing that compound or its salt to $$R-\underset{N=}{\overset{N-}{\diagup}}\!\!\diagdown\!\!-OH \quad (V)$$

and phosphorylating. Several of the intermediates are new.

6 Claims, No Drawings

PREPARATION OF PHOSPHORIC ACID DERIVATIVES AND INTERMEDIATES

The invention relates to a new process for the preparation of insecticidal pyrimidinylphosphoric acid derivatives, intermediates which can be used for carrying out the process, and processes for the preparation of such intermediates.

It has already been disclosed that certain pesticidal phosphoric acid pyrimidine esters are obtained when corresponding chlorophosphoric acid esters are reacted with 5-hydroxypyrimidines (compare U.S. Pat. No. 4,127,652, DE-OS (German Published Specification) 2,706,127 and U.S. Pat. No. 4,686,290. However, a need for new readily available intermediates exists, which can be employed in a preparation process for phosphoric acid pyrimidine esters which can easily be carried out.

It has now been found that the compounds of the general formula (I)

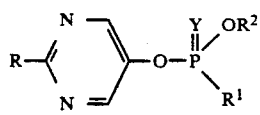  (I)

in which
R stands for hydrogen, alkoxy, alkylamino, dialkylamino or for optionally substituted radicals from the series comprising alkyl, cycloalkyl, aralkyl and aryl,
$R^1$ stands for optionally substituted radicals from the series comprising alkyl, alkoxy, alkylthio, mono- or dialkylamino and phenyl,
$R^2$ stands for optionally substituted alkyl
and are obtained
when
(a1) compounds of the general formula (IIa)

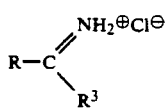  (IIa)

in which
R has the abovementioned meaning,
$R^3$ stands for amino or the group $XR^4$, where
X stands for oxygen or sulphur and
$R^4$ stands for methyl or ethyl, are reacted with 1,3-diamino-2-propanol of the formula (III)

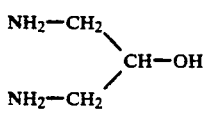  (III)

or its acid addition salts, if appropriate in the presence of diluents at temperatures between 0° C. and 120° C.;
(a2) or when carboxylic acids of the formula (IIb)

$R^5—CO_2H$  (IIb)

in which
$R^5$ has the abovementioned meaning for R, excluding hydrogen, are reacted with 1,3-diamino-2-propanol of the formula (III)

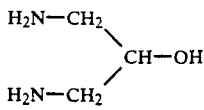  (III)

if appropriate in the presence of diluents at temperatures between 120° C. and 250° C.; or
(a3) when carboxylic acid salts of 1,3-diamino-2-propanol of the formula (IIc)

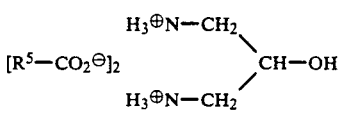  (IIc)

in which
$R^5$ has the abovementioned meaning, are heated at temperatures between 120° C. and 250° C., and the 5-hydroxy-3,4,5,6-tetrahydropyrimidine salts formed of the general formula (IV)

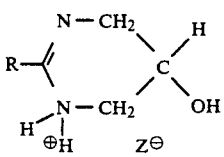  (IV)

in which
Z stands for chlorine or $R^5—CO_2$, where $R^5$ has the abovementioned meaning and
R has the abovementioned meaning are optionally isolated and
(b) the 5-hydroxy-3,4,5,6-tetrahydropyrimidines of the general formula (IVa)

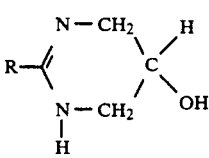  (IVa)

in which
R has the abovementioned meaning, are optionally released therefrom using a base and subsequently
(c) either
the 5-hydroxy-3,4,5,6-tetrahydropyrimidine hydrochlorides of the general formula (IV)

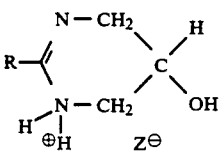  (IV)

in which
Z stands for chlorine or $R^5—CO_2$, where $R^5$ has the abovementioned meaning and
R has the abovementioned meaning or the free 5-hydroxy-3,4,5,6-tetrahydropyrimidines of the general formula (IVa)

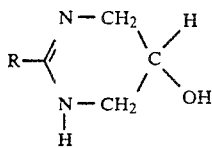

(IVa)

in which

R has the abovementioned meaning, are optionally oxidized or dehydrogenated after their isolation to give the compounds of the general formula (V)

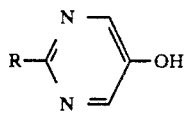

(V)

in which

R has the abovementioned meaning, and subsequently (d) the compounds of the formula (V), optionally after their isolation, are reacted with compounds of the general formula (VI)

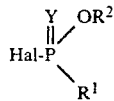

(VI)

in which

Hal stands for halogen and

Y, $R^1$ and $R^2$ have the abovementioned meaning, if appropriate in the presence of an acid-binding agent and if appropriate in the presence of a solvent, and the compounds of the general formula (I) are isolated.

According to this process, it is possible to prepare the compounds of the formula (I) in a simple manner in good purity and yield. The process is very widely utilizable in regard to the type of substituents desired. Furthermore, the compounds to be employed as intermediates are stable and can be easily stored and handled.

Preferred substituents or ranges of the radicals shown in the formulae mentioned above and below are illustrated in the following:

Alkoxy R stands for straight-chain or branched alkoxy preferably having 1 to 12, in particular 1 to 6 and particularly preferably 1 to 4 carbon atoms. Methoxy, ethoxy, n-propoxy, i-propoxy, n-butoxy, i-butoxy, sec-butoxy and tert-butoxy may be mentioned as examples.

Mono- or di-alkylamino R stands for an amino group having 1 or 2 alkyl groups, preferably 2 alkyl groups, which can each be straight-chain or branched and preferably contain 1 to 5, in particular 1 to 3 carbon atoms, where methyl, ethyl, n- and i-propyl may be mentioned. Dimethylamino, diethylamino, di-n-propylamino and di-i-propylamino may be mentioned as examples.

Optionally substituted alkyl R stands for straight-chain or branched alkyl having 1 to 20, preferably 1 to 12, in particular 1 to 6 and particularly preferably 1 to 4 carbon atoms. Substituted methyl, ethyl, n-propyl, i-propyl, n-butyl, sec-butyl, i-butyl, tert-butyl, n-pentyl, i-pentyl and tert-pentyl may optionally be mentioned as examples.

Optionally substituted cycloalkyl R stands for cycloalkyl preferably having 3 to 8, in particular 3, 5 or 6 carbon atoms. Substituted cyclopropyl, cyclobutyl, cyclopentyl, cyclohexyl and cycloheptyl may optionally be mentioned as examples.

Optionally substituted aralkyl preferably contains 1 to 4 carbon atoms in the straight-chain or branched alkyl moiety and phenyl as the aryl moiety. Benzyl which is preferably unsubstituted may be mentioned as an example of an aralkyl group.

Optionally substituted aryl R stands for aryl preferably having 6 to 10 carbon atoms in the aryl moiety. Substituted phenyl or naphthyl, in particular phenyl, may optionally be mentioned as an example.

The substituted radicals mentioned in the definition of R can carry one or more, preferably 1 to 3, in particular 1 or 2 identical or different substituents. Substituents for alkyl, cycloalkyl and aryl which may be mentioned as examples are:

Alkoxy and alkylsulphonyl having 1 to 4 carbon atoms, such as methoxy, ethoxy, n-propoxy, i-propoxy, n-butoxy, i-butoxy, sec-butoxy, tert-butoxy, methylsulphonyl, ethylsulphonyl, n-propylsulphonyl, i-propylsulphonyl, n-butylsulphonyl, i-butylsulphonyl and tert-butylsulphonyl.

Suitable aryl substituents and cycloalkyl substituents are, in addition, $C_1$-$C_4$-alkyl ethyl, n-propyl, i-propyl, n-butyl, i-butyl, sec-butyl and tert-butyl. Preferably, the radicals R are unsubstituted.

R preferably stands for hydrogen, for alkoxy having 1 to 12 carbon atoms, for mono- or di-alkylamino each having 1 to 6 carbon atoms in the alkyl moiety, for alkyl having 1 to 12 carbon atoms which is optionally substituted by $C_1$-$C_4$-alkoxy or $C_1$-$C_4$-alkylsulphonyl, for cycloalkyl having 3 to 8 carbon atoms which is optionally substituted by $C_1$-$C_4$-alkyl, and for benzyl or aryl having 6 to 10 carbon atoms which are optionally substituted by $C_1$-$C_4$-alkyl, $C_1$-$C_4$-alkoxy or $C_1$-$C_4$-alkylsulphonyl.

R particularly preferably stands for hydrogen, alkoxy having 1 to 6 carbon atoms, mono- or di-alkylamino each having 1 to 4 carbon atoms in the alkyl moiety or for alkyl having 1 to 6 carbon atoms which is optionally substituted by methoxy, ethoxy, methylsulphonyl or ethylsulphonyl, for cycloalkyl having 3 to 6 carbon atoms which is optionally substituted by methyl or ethyl, and for benzyl or phenyl which is optionally substituted by methyl, ethyl, methoxy, ethoxy, methylsulphonyl or ethylsulphonyl.

R very particularly preferably stands for methyl, isopropyl and tert-butyl (preferably tert.-butyl).

$R^5$ has the same general and preferred meanings as R, where, however, hydrogen is excluded.

The optionally substituted alkyl groups $R^1$ and $R^2$ preferably contain 1 to 6, in particular 1 to 4 and particularly preferably 1 or 2 carbon atoms.

Methyl, ethyl, n- and i-propyl, n-, i-, s- and t-butyl (preferably ethyl and s-butyl) may be mentioned as examples.

The alkyl groups of the optionally substituted alkyl- and dialkylamino groups $R^1$ preferably have the preferred meaning mentioned above for the alkyl groups $R^1$ and $R^2$ Methyl-, ethyl-, n- and i-propylamino and also dimethyl-, diethyl- and methylethylamino may be mentioned as examples.

The alkoxy- and alkylthio radicals $R^1$ preferably contain 1 to 6, in particular 1 to 4 and particularly preferably 1 or 2 carbon atoms. Methoxy, ethoxy, n- and i-propoxy and also methylthio, ethylthio and n- and ipropylthio (preferably ethoxy) may be mentioned as examples.

The optionally substituted radicals $R^1$ and $R^2$ can carry one or more, preferably 1 or 3, in particular 1 or 2 identical or different substituents. Substituents which may be mentioned as examples are: alkyl (does not apply for the cases in which $R^1$ or $R^2$ stands for alkyl) preferably having 1 to 4, in particular 1 or 2 carbon atoms, such as methyl, ethyl, n- and i-propyl, and n-, i-, s- and t-butyl; alkoxy preferably having 1 to 4, in particular 1 or 2 carbon atoms, such as methoxy, ethoxy, n-and i-propoxy and n-, i-, s- and t-butoxy; alkylthio preferably having 1 to 4, in particular 1 or 2 carbon atoms, such as methylthio, ethylthio, n- and i-propylthio and n-, i-, s- and t-butylthio; halogen, preferably fluorine, chlorine, bromine and iodine, in particular chlorine and bromine; cyano and nitro. Preferably, the radicals $R^1$ and $R^2$ are unsubstituted.

Hal in the general formula (VI) stands for fluorine, chlorine, bromine and iodine, preferably for fluorine, chlorine and bromine, in particular for chlorine.

Y preferably stands for sulphur and X preferably stands for oxygen.

The formula (IIa), (IIb) or (IIc) provides a general definition of the compounds to be used as starting materials in process step (a). In this formula, R preferably has the meanings that have already been mentioned as preferred for these substituents in connection with the description of the substances of the formula (I).

The following compounds may be mentioned as examples of the compounds of the formula (IIa) in which $R^3$ stands for amino:

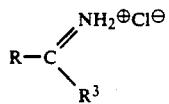

TABLE 1

| R | R |
|---|---|
| H | $OC_2H_5$ |
| $CH_3$ | $OC_3H_7$-n |
| $C_2H_5$ | $OC_3H_7$-i |
| $C_3H_7$-n | $-CH_2OCH_3$ |
| $C_3H_7$-i | $-CH_2CH_2OCH_3$ |
| $C_4H_9$-n | $-CH_2OC_2H_5$ |
| $C_4H_9$-i | $-CH_2CH_2OC_2H_5$ |
| $C_4H_9$-s | $-CH_2SO_2CH_3$ |
| $C_4H_9$-t | $-CH_2CH_2SO_2CH_3$ |
| $C_5H_{11}$-n | $-CH_2CH_2SO_2C_2H_5$ |
| $C_5H_{11}$-t | $-N(CH_3)_2$ |
| $OCH_3$ | $-N(C_2H_5)_2$ |

 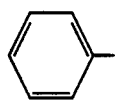

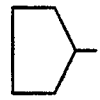 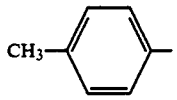

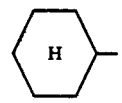

The compounds of the formula (IIa) are generally known or can be prepared by known processes (compare Org. Synthesis Coll. Vol. I, p. 5 (1951); Beilstein vol. 2, p.185; vol.2/III, p. 452; vol. 2/III, p 478; vol. 9, p. 280; US-PS 4,012,506).

Formula (IIa) likewise provides a general definition of the iminoalkyl(thio)ether hydrochlorides to be used as starting materials in process step (a). In this formula, $R^3$ stands for the group $XR^4$, and X and $R^4$ preferably have the meanings which have already been mentioned as preferred for X and $R^4$ in connection with the description of the substances of the formula (III).

Examples of the compounds of the formula (IIa) in which $R^3$ stands for $XR^4$.

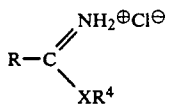

and also for the compounds of the formula (IIb)

$$R^5-CO_2H \qquad (IIb)$$

which may be mentioned are:

TABLE 2

| R or $R^5$ | R or $R^5$ |
|---|---|
| H (for formula IIa) | $OC_2H_5$ |
| $CH_3$ | $OC_3H_7$-n |
| $C_2H_5$ | $OC_3H_7$-i |
| $C_3H_7$-n | $-CH_2OCH_3$ |
| $C_3H_7$-i | $-CH_2CH_2OCH_3$ |
| $C_4H_9$-n | $-CH_2OC_2H_5$ |
| $C_4H_9$-i | $-CH_2CH_2OC_2H_5$ |
| $C_4H_9$-s | $-CH_2SO_2CH_3$ |
| $C_4H_9$-t | $-CH_2CH_2SO_2CH_3$ |
| $C_5H_{11}$-n | $-CH_2CH_2SO_2C_2H_5$ |
| $C_5H_{11}$-t | $-N(CH_3)_2$ |
| $OCH_3$ | $-N(C_2H_5)_2$ |

 

 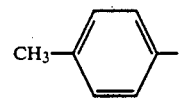

 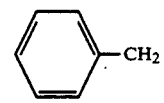

The iminoalkyl(thio)ether hydrochlorides of the formula (IIa) are generally known compounds of organic chemistry, or can be prepared by known processes (compare Org. Synthesis Coll. Vol. I, p. 5 (1951); Beilstein Vol. 2, p. 182; Vol. 2, p. 245; Vol. 2/III, p. 451; Vol. 2/III, p. 618; Vol. 2/III, p. 675; U.S. Pat. No. 4,012,506).

1,3-Diamino-2-propanol of the formula (III) to be used as a starting material in process step (a) is known (compare U.S. Pat. No. 3,432,553). The acid addition salts of the formula (III) alternatively to be used as starting materials in process step (a) are generally known compounds of organic chemistry. Examples which may be mentioned are: 1,3-diamino-2-propanol hydrochloride or -di-p-toluenesulphonate, 1,3-diamino- 2-propanol dihydrochloride or -di-picrate, 1,3-diamino-2-propanol dihydrobromide, 1,3-diamino-2-propanol sulphate, etc.

The salts of the compound of the formula (III) with the carboxylic acids of the formula (IIb) can be obtained by the generally customary salt-formation methods.

Process step (a1) according to the invention for the preparation of the compounds of the general formula (IV) is preferably carried out in the presence of diluents. Suitable diluents are preferably:

Alcohols, such as methanol, ethanol, n- and i-propanol, tert-butanol, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, nitriles, such as, for example, acetonitrile and propionitrile, amides, such as, for example, dimethylacetamide and n-methyl-pyrrolidone, and tetramethylenesulphone.

The reaction temperature can be varied within a relatively wide range in process step (a1). In general, the reaction is carried out between 0° C. and +120° C., preferably at +40° C. to +80° C. The process according to the invention is in general carried out at atmospheric pressure.

To carry out the process (a1) according to the invention, the starting materials are customarily employed in equimolar amounts. An excess of one or the other reaction components carries no substantial advantages. The working up and also the optionally desired isolation takes place by customary methods, for example by distilling of the solvent under reduced pressure, as a result of which the product of the formula (IV) is present as a residue.

Surprisingly, the new 5-hydroxy-3,4,5,6-tetrahydropyrimidine hydrochlorides of the general formula (IV) can be obtained very easily and in good yields and also in high purity by the process (a1) according to the invention. They are therefore especially suitable for employing in the process steps (b) and (c).

If, for example, isobutyramidine hydrochloride and 1,3-diamino-2-propanol are used as starting materials in process step (a1) according to the invention for the preparation of the compounds of the general formula (IV), then the reaction can be outlined by the following equation:

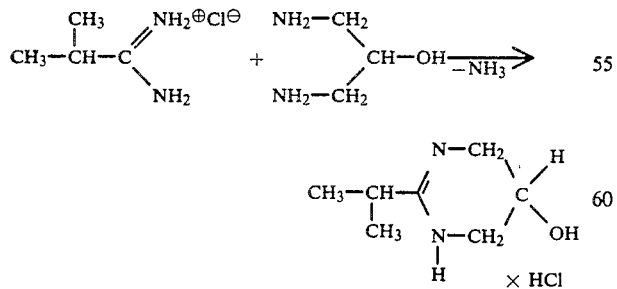

The process steps (a2) and (a3) according to the invention for the preparation of the compounds of the general formula (IV) are preferably carried out in the presence of diluents which form an azeotrope with water. The water formed during the reaction is preferably continuously removed from the reaction batch.

Suitable diluents are preferably: chlorobenzene, o-dichlorobenzene, xylenes (ortho, meta, para, or mixtures), toluene, methylcyclohexane, decahydronaphthalene, anisole, ethylbenzene or isopropylbenzene.

The reaction temperature is in general between 120° C. and 250° C. In order to avoid far too long reaction times, the reaction is expediently carried out above 135° C., preferably between 135° C. and 200° C.

The reaction can be carried out at normal pressure, but also at elevated or reduced pressure.

When carrying out process step (a2), 1.5 to 3, preferably 2 to 2.5 moles, of the carboxylic acid of the formula (IIb) are employed per mole of diaminopropanol of the formula (III) or its carboxylic acid salt.

The working up and isolation of the compounds of the formula (IV) takes place by filtering off or separating off the phase formed which contains the compounds of the formula (IV).

If, for example, isobutyric acid and 1,3-diamino-2-propanol are used as starting materials in process step (a2) according to the invention, then the first step of the reaction can be outlined by the following equation:

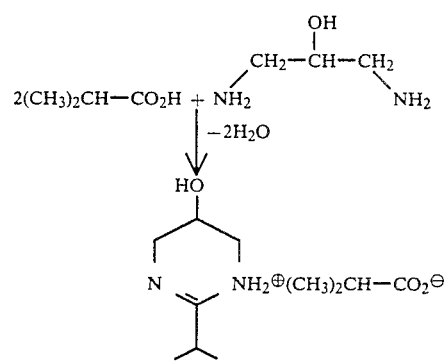

If, for example, the di-pivalate salt of 1,3-diamino-2-propanol is used as starting material in process step (a3) according to the invention, then the reaction can be outlined by the following equation:

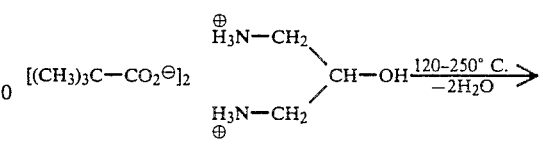

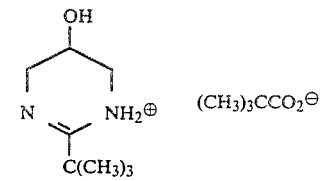

Surprisingly, the 5-hydroxy-3,4,5,6-tetrahydropyrimidine derivatives of the formula (IV) can be obtained in good yields and high purity by process step (a2) according to the invention.

In particular, it was not expected by the person skilled in the art that the carboxylic acids of the formula (IIb) would react while at relatively low temperature, since it was known from the literature that an analogous reaction with diaminopropane requires temperatures of 225° C. (EP-PS 117,882).

Moreover, in order to obtain monoacylation, diaminopropane is preferably employed in a large excess in the patent application mentioned. It is thus extremely surprising to see that the reaction proceeds in such good yield in spite of employment of excess carboxylic acid of the formula (IIb).

The process according to the invention is furthermore to be designated as decidedly surprising since the person skilled in the art would expect possible dehydration of the secondary alcohol group or esterification of the alcohol group with the carboxylic acids of the formula (IIb) under the acidic reaction conditions.

In process variant (a3), the process conditions (solvents, temperatures, working up and isolation) are carried out as in process (IIb).

The following compounds may be mentioned as examples of the compounds of the formula (IV) which can be obtained according to the invention:

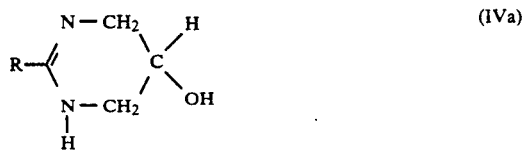

$Z = Cl, R^5CO_2$

TABLE 3

| R or $R^5$ | R or $R^5$ |
|---|---|
| H (Z = Cl) | $OC_2H_5$ |
| $CH_3$ | $OC_3H_7$-n |
| $C_2H_5$ | $OC_3H_7$-i |
| $C_3H_7$-n | $-CH_2OCH_3$ |
| $C_3H_7$-i | $-CH_2CH_2OCH_3$ |
| $C_4H_9$-n | $-CH_2OC_2H_5$ |
| $C_4H_9$-i | $-CH_2CH_2OC_2H_5$ |
| $C_4H_9$-s | $-CH_2SO_2CH_3$ |
| $C_4H_9$-t | $-CH_2CH_2SO_2CH_3$ |
| $C_5H_{11}$-n | $-CH_2CH_2SO_2C_2H_5$ |
| $C_5H_{11}$-t | $-N(CH_3)_2$ |
| $OCH_3$ | $-N(C_2H_5)_2$ |

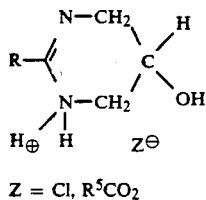

The process for the preparation of the compounds of the general formula (IV) according to process step (a1), (a2) and (a3) is not yet known from the literature and is part of the present invention. Similarly, the compounds of the general formula (IV), excluding the compounds in which R denotes hydrogen, methyl or chloromethyl and Z denotes chlorine, are new and a part of the present invention.

These compounds can be employed, for example, in process step (c).

Some of the compounds of the general formula (IVa) likewise to be employed in process step (c) are known. Thus, it is already known that 1,3-diamino-propan-2-ol condenses with ethyl formate to give 5-hydroxy-3,4,5,6-tetrahydropyrimidine and gives 5-hydroxy-2-methyl-3,4,5,6-tetrahydropyrimidine with ethyl acetate (compare J. Org. Chem., 3838–3839, (1966)). The disadvantages of this process consist in the moderate yields and the complicated working up of the final products.

It has now been found that 5-hydroxy-3,4,5,6-tetrahydropyrimidines of the general formula (IVa)

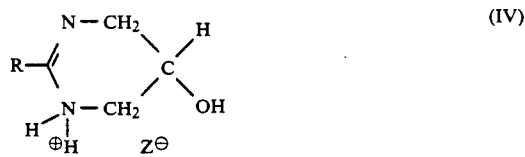

in which

R has the abovementioned meaning, are obtained when 5-hydroxy-3,4,5,6-tetrahydropyrimidine hydrochlorides of the general formula (IV)

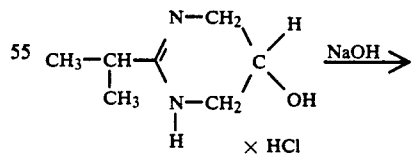

in which

R and Z have the abovementioned meanings, are reacted with a base, preferably with an aqueous solution of alkali metal hydroxide, in particular sodium hydroxide and/or potassium hydroxide.

It is surprising to note that the new 5-hydroxy-3,4,5,6-tetrahydropyrimidines are obtained in good yields and in high purity in a technically simple manner by process (b) according to the invention, since it was known that 3,4,5,6-tetrahydro-5-hydroxypyrimidine and 3,4,5,6-tetrahydro-2-methyl-5-hydroxypyrimidine are very easily hydrolyzed.

If, for example, 3,4,5,6-tetrahydro-2-isopropyl-5-pyrimidinol hydrochloride is used as a starting material and sodium hydroxide is used as a base in process step (b) according to the invention, then the reaction can be outlined by the following equation:

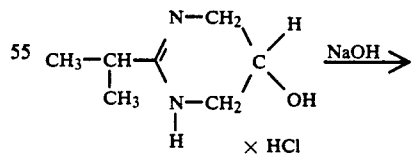

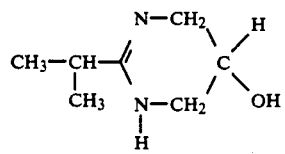

The free bases of the compounds of the formula IV indicated in Table 3 may be mentioned as examples of the compounds of the formula (IVa) which can be obtained according to the invention.

When carrying out the process according to the invention for the preparation of the compounds of the general formula (IVa), the starting material of the formula (IV) is preferably initially introduced into water and the aqueous alkaline solution (preferably sodium hydroxide solution or potassium hydroxide solution) is added dropwise.

When carrying out process step (b) according to the invention, 1 to 2 moles, preferably 1 to 1.5 moles, of alkaline solution are reacted with 1 mole of starting material of the formula (IV).

The reaction is carried out at room temperature or slightly elevated temperatures. In general, the reaction is carried out between 10° C. and 50° C., preferably, however, between 10° C. and 30° C. In particular, the reaction is carried out at room temperature.

The concentration of the aqueous alkali metal hydroxide solution can be between 10% and 50%, preferably, however, between 20% and 45%. (The percentage data relate to percentages by weight.)

The working up and optionally desired isolation of the compounds of the general formula (IVa) takes place by customary methods, such as, for example, by filtering off with suction.

The compounds of the general formula (IVa) can also be obtained from the salts of the formula (IV) with the aid of strongly basic ion exchangers. For this, customary (commercially available) ion exchangers can be used. The reaction takes place by customary methods. Preferably, aqueous solutions of the compounds of the formula (IV) are stirred with a sufficient amount of ion exchanger, the ion exchanger is filtered off and the water is removed from the filtrate (for example by carefully distilling off as much as possible or with very sensitive bases by freeze-drying).

The compounds of the general formula (V) to be employed in process step (d) are known or can be prepared by generally known methods.

Thus, it is already known that 5-hydroxy-pyrimidines are obtained when 5-methoxy-pyrimidines are reacted under basic conditions in an autoclave, at temperatures between 180° C. and 200° C. (compare, for example, DE-OS (German Published Specification) 2,643,262 and Coll. Czech. Chem. Comm. 40, 1078 ff (1975)). The disadvantages of this process are that the yields and the purity of the reaction products are frequently unsatisfactory and, in addition, extreme reaction conditions are necessary.

In addition, it is known that 5-hydroxy-pyrimidines can also be prepared from 5-methoxy-pyrimidines in the presence of alkali metal hydroxides and glycol. In this process, temperatures of about 200° C. are necessary. Further disadvantages are the complicated work-up of the final products and the moderate yields (compare, for example, J. Chem. Soc. 1960, 4590 ff and Chem. Ber. 95, 803 ff (1962)). In addition, the procedure in polar high-boiling solvents such as glycol demands particular efforts for waste water purification.

Furthermore, it is known that 5-hydroxy-pyrimidines can also be prepared from 4-chloro-pyrimidine derivatives using hydrogen in the presence of hydrogenation catalysts. The disadvantage of this process lies in the complicated preparation of the 4-chloropyrimidines (compare DE-OS (German Published Specification) 3,423,623).

It has been found that the 5-hydroxy-pyrimidines of the general formula (V)

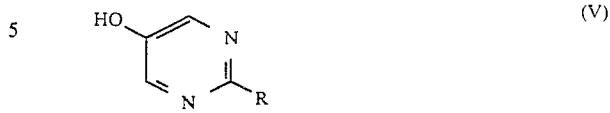

in which

R has the abovementioned meaning, are obtained when either substituted 5-hydroxy-3,4,5,6-tetrahydropyrimidine salts of the general formula (IV)

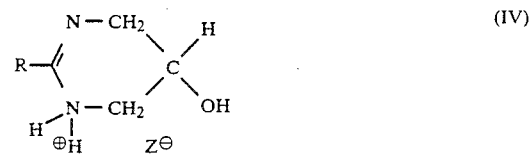

in which

R and Z have the abovementioned meanings, or 5-hydroxy-3,4,5,6-tetrahydropyrimidines of the general formula (IVa)

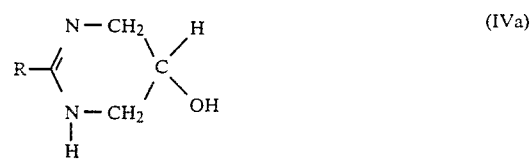

in which

R has the abovementioned meaning, are reacted, optionally after their isolation, with oxidants, if appropriate in the presence of dehydrogenation catalysts and if appropriate in the presence of diluents at temperatures between 5° C. and 150° C.

Surprisingly, it is possible with the aid of this process, which corresponds to process step (c) and which is a part of the present invention, to obtain the 5-hydroxypyrimidines of the general formula (V) in very high purity under relatively mild conditions. Further advantages of the process are the recovery of the catalysts and the use of inexpensive and more environmentally beneficial diluents.

If, for example, 3,4,5,6-tetrahydro-2-tert-butyl-5-hydroxypyrimidine is used as the starting material and oxygen as the oxidant in the process according to the invention, then the reaction can be outlined by the following equation:

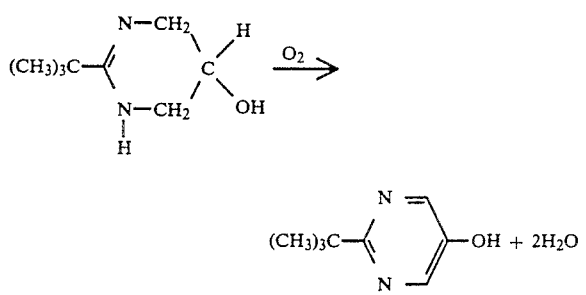

For the preparation of the compounds of the general formula (V) from the compounds of the general formula (IV) and (IVa), water is preferably used as the solvent.

The oxidants or dehydrogenation agents for the process according to the invention are known per se (Organikum, VEB Deutscher Verlag der Wissenschaften, Berlin 1977, pages 430–471). For example nitric acid, oxygen and its per compounds (hydrogen peroxide, metal peroxide, inorganic and organic per acids), sulphur, selenium dioxide, chlorine, bromine, hypohalous acids, chloric acid, periodic acid, metal compounds of higher valency states [iron(II) compounds, manganese dioxide, potassium permanganate, chromic acid, chromic anhydride, lead dioxide and lead tetraacetate], tetrachloro-p-benzoquinone and dichlorodicyanobenzoquinone (DDQ) may be mentioned. Preferred oxidants are potassium permanganate, ammonium peroxodisulphate, sodium peroxodisulphate or potassium peroxodisulphate and chromium trioxide.

It can also be advantageous to carry out the process according to the invention in the presence of dehydrogenation catalysts. Preferably, metal catalysts of the VIIIth subgroup of the periodic table, such as, for example, platinum or paladium, if appropriate on customary support materials, such as, for example, active carbon, silica or alumina.

The reaction temperatures can be varied within a relatively wide range when carrying out the process according to the invention. In general, the reaction is carried out at temperatures between $+10°$ C. and $+180°$ C., preferably at temperatures between $+20°$ C. and $+150°$ C., in particular between $+20°$ C. and $+100°$ C.

The process according to the invention is in general carried out at atmospheric pressure. Under certain prerequisites, in particular when using dehydrogenation catalysts, it can be advantageous, however, also to work under elevated pressure.

To carry out the process according to the invention, between 0.5 and 5 moles, preferably between 0.6 and 4 moles of oxidant and/or between 0.01 and 1 mole, preferably between 0.05 and 0.5 moles, of dehydrogenation catalyst are in general employed per mole of 5-hydroxy-3,4,5,6-tetrahydropyrimidine or hydrochloride of the formula (IV) or (IVa).

In a particularly preferred embodiment, the oxidation (dehydrogenation) of the compounds of the general formula (IV) and (IVa) to give the compounds of the general formula (V) is carried out using oxygen as the oxidant. In a very particularly preferred embodiment variant, the dehydrogenation using oxygen (air) is carried out in the liquid phase in the presence of a solvent and a base. The addition of a heavy metal salt (preferably a transition metal compound) proves advantageous.

By these process variants of process step (c), it is surprisingly possible to prepare the 5-hydroxypyrimidines in particularly high yield and high purity. This process step is furthermore characterized by the easy availability of the starting components, by a cheap and easy to handle oxidant, by mild reaction conditions and by a very simple work-up.

Solvents for the process according to the invention for the preparation of (V) by dehydrogenation of (IV) or (IVa) using oxygen in process step (c) are those which react only comparatively slowly or not at all with oxygen and which at least partly dissolve the starting materials. Examples which may be mentioned are: alcohols, ether alcohols, hydrocarbons, fluorinated hydrocarbons, amines, nitriles, amides, ethers, polyethers, esters, sulphoxides, sulphones, lactones, lactams etc. Of these, alcohols, ether alcohols, amines, sulphoxides, sulphones, amides, ethers and polyethers, in particular alcohols, amines, amides, sulphoxides and sulphones are preferably employed. Individual examples of the range of alcohols and ether alcohols are: methanol, ethanol, n- and i-propanol, 1-butanol, 2-butanol, tert.-butanol, isopentyl alcohol, isohexanol, isooctanol, diethylene glycol, tetraethylene glycol, etc. examples of the range of amines which may be mentioned are: triethylamine, dibutylamine, ethylenediamine, tetramethylethylenediamine, permethyldiethylenetriamine, pyridine, picoline, quinoline, dimethylaniline, diphenylamine, di- and tribenzylamine. Individual examples of the range of sulphoxides and sulphones are dimethyl sulphoxide, methyl phenyl sulphoxide, dimethylsulphone etc. Individual examples at the range of amides are formamide, acetamide, dimethylformamide, dimethylacetamide, N-methylpyrrolidone,etc. Individual examples of the range of ethers and polyethers are: methyl tert.butyl ether, di-tert.-butyl ether, diethylene glycol dimethyl ether, triethylene glycol dimethyl ether etc. The solvents t-butanol, dimethyl sulphoxide and the amines and amides mentioned, in particular dimethylformamide, N-methylpyrrolidone, pyridine and picoline, and also mixtures of these solvents, are particularly preferred.

A variety of the known bases such as amines, metal carbonates, metal hydroxides, metal alkoxides, metal amides, quaternary ammonium hydroxide, etc.,are suitable as bases for dehydrogenation using oxygen. The choice of the base in particular depends on the choice of the reaction conditions such as solvent and reaction temperature.

The hydroxides, alkoxides and amides of the alkali metals and alkaline earth metals and of aluminum are preferably employed. In this connection, particularly preferable alkali metals and alkaline earth metals are sodium, potassium, lithium, magnesium, calcium and barium. Examples of alkoxides which may be mentioned are the methoxide, ethoxide, isopropoxide, sec.-butoxide, tert.-butoxide and the salt of tetraethylene glycol. The amides can, for example, be unsubstituted amide, ethylamide, diethylamide, diisopropylamide, dibutylamide, etc. Of the bases mentioned, hydroxides and alkoxides are preferred, sodium hydroxide, potassium hydroxide, sodium methoxide, sodium ethoxide and potassium tert.-butoxide being particularly preferred. Preferred bases are likewise quaternary ammonium hydroxide, such as, for example, tetramethyl ammonium hydroxide and strongly basic ion exchange resins, such as, for example, those containing quaternary ammonium hydroxide as the functional group. The base can optionally also be employed in combination with a crown ether, for example, 18-crown-6.

The base is employed in an amount of 1–15 equivalents per mole of the 5-hydroxy-tetrahydropyrimidine (IV) or (IVa), preferably 1–10 equivalents, particularly preferably 2–7 equivalents.

Advantageously, but not absolutely necessarily, heavy metal salts, preferably transition metal compounds, are added as catalysts to the reaction mixture in the process according to the invention for the preparation of compounds of the formula (V) by oxidation of compounds of the formula (IV) or compounds of the formula (IVa) using oxygen in process step (c). Those transition metals which are known to catalyze oxidations, autoxidations and dehydrogenations, for example vanadium, chromium, manganese, iron, cobalt, nickel, copper, silver, niobium, ruthenium, molybdenum, palladium, tungsten and platinum prove effective. Under these, copper, manganese, cobalt, nickel, iron and ruthenium are preferred, copper, cobalt and manganese being particularly preferred and copper being very particularly preferred. These metals can be added individually or in suitable combinations and to any of the individually possible oxidation steps.

Possible use forms of such metal compounds are the metal salts of inorganic acids, for example the halides such as fluorides, chlorides, bromides or iodides, the sulphates, nitrates, carbonates, phosphates, borates, sulphites, cyanides or the salts of organic acids, such as the acetates, stearates, oxalates or ion exchangers which contain those metals bonded. Furthermore, metal complexes or complex salts, for example amine complexes, halogen complexes and metal chelate complexes for example metal acetylacetonates, metal glyoximates, metal phthalocyanines, metal porphyrins or metal complexes with the ligand bis-salicylaldehyde-ethylenediamine can also be employed. The metals can, however, also be added to the reaction mixture in elementary form.

In a preferred manner, the metal compounds are used in the form of the salts of inorganic or organic acids (particularly preferably inorganic acids), in particular as chlorides, sulphates, nitrates, oxides, hydroxides, acetates, etc., in hydrated or dehydrated form. In a particularly preferred manner, inorganic and organic salts of copper are employed, for example $CuO$, $CuCl_2 \cdot 2 H_2O$, $CuSO_4$, $Cu(OAc)_2$, $CuCl$, etc.

The amount of metal catalyst employed is subjected to no specific limitation. Any suitable amount, as long as it does not exceed 0.0001 mole equivalents, relative to the compounds of the formula (IV) or (IVa), is effective. The range from 0.0005–0.10 is preferred, the range from 0.001–0.05 mole equivalents, relative to the compounds of the formula (IV) or (IVa) being particularly preferred.

Pure oxygen or oxygen in dilute form, for example in the form of oxygen-containing gases, preferably air or oxygen/nitrogen mixtures, can be employed as oxygen for the process according to the invention for the preparation of compounds of the formula (V) by oxygen oxidation of compounds of the formula (IV) or (IVa) in process step (c). Atmospheric air is the most economically favorably form of oxygen utilizable according to the invention. The pressure of the oxygen or the oxygen-containing gas is subjected to no particular limitation and can lie between 1–100 bar, preferably at 1–10 bar. The oxygen content is likewise subjected to no limitation when using oxygen-containing gases. It preferably depends on operational points of view, such as operational safety and the rate of reaction. The addition of oxygen to the reaction medium can take place, for example, using frits; it can, however, be absorbed in the reaction mixture by vigorous stirring.

The reaction temperature can vary within wide limits and is preferably 0–300° C., particularly preferably 20°–200° C. and very particularly preferably 40° to 120° C.

The oxidation of the compounds of the formula (IV) or (IVa) to give compounds of the formula (V) using oxygen by the process according to the invention is preferably carried out in the liquid phase. The liquid and solid starting components can either be added together completely at the beginning Df the reaction, or, however, one or more components, for example the base and/or the compounds of the formulae (IV) or (IVa), can be metered in during the reaction optionally with the aid of a solvent.

The type of work-up in connection with the process according to the invention for the preparation of the compounds of the formula (V) by oxygen oxidation takes place by the customary methods. It depends on the particular experimental conditions. If the reaction was carried out in the presence of a metal catalyst, then a substantial recovery of the metal is indicated for reasons of environmental protection. Since the oxidation takes place in alkaline medium in the process according to the invention, the metal compounds, insofar as they are employed as oxides or salts, are present as oxide hydrates after the hydrolysis of the reaction mixture. The metals can be filtered off, for example, directly from the reaction mixture, in the form of their oxide hydrates, where, when required, this was sufficiently dilute in order to dissolve starting materials and products. The filtrate can subsequently be evaporated, the residue taken up in water and the 5-hydroxypyrimidine released by acidifying.

In a work-up variant, the solvent can be evaporated off from the reaction mixture, the residue taken up in water and the insoluble metal oxide hydrate filtered off. This procedure is possible since both the products and the by-products formed are excellently soluble in aqueous alkaline solution. The 5-hydroxypyrimidine can be released from the filtrate again by acidifying.

In a still further work-up variant, water can be added directly to the reaction mixture and the insoluble oxide hydrate filtered off. The organic solvent is separated off from the filtrate, for example, by distillation or extraction and the 5-hydroxypyrimidine is released from the aqueous alkaline solution by acidifying.

If the solvent used in the process according to the invention is water-insoluble, then water can be added to the reaction mixture, the organic part can be separated off and optionally recycled. The metal oxide hydrate is subsequently removed from the aqueous alkaline solution by filtration and the 5-hydroxypyrimidine is released from the filtrate by acidifying.

The 5-hydroxypyrimidine released after acidifying the aqueous alkaline solution can be isolated according to the known methods, for example by filtration and/or extraction and can be subsequently purified, for example by distillation and/or crystallization.

The following may be mentioned as examples of the compounds of the general formula (V) which can be obtained according to the invention:

TABLE 5

$$HO-\underset{N}{\overset{N}{\diagdown}}-R \quad (V)$$

| R | R |
|---|---|
| H | $-OC_2H_5$ |
| $-CH_3$ | $-OC_3H_7$-n |
| $-C_2H_5$ | $-OC_3H_7$-i |
| $-C_3H_7$-n | $-CH_2OCH_3$ |
| $-C_3H_7$-i | $-CH_2CH_2OCH_3$ |
| H | $-OC_2H_5$ |
| $-C_4H_9$-n | $-CH_2OC_2H_5$ |
| $-C_4H_9$-i | $-CH_2CH_2OC_2H_5$ |
| $-C_4H_9$-s | $-CH_2SO_2CH_3$ |
| $-C_4H_9$-t | $-CH_2CH_2SO_2CH_3$ |
| $-C_5H_{11}$-n | $-CH_2CH_2SO_2C_2H_5$ |
| $-C_5H_{11}$-t | $-N(CH_3)_2$ |
| $-OCH_3$ | $-N(C_2H_5)_2$ |

TABLE 5-continued $$HO-\underset{N}{\underset{\|}{\overset{N}{\overset{\|}{\diagup}}}}-R \quad (V)$$

| R | R |
|---|---|
| CH₂<br>\|  \CH—<br>CH₂/ | ⟨phenyl⟩ |
| ⟨cyclopentyl⟩ | ⟨4-methylphenyl⟩—CH₃ |
| ⟨cyclohexyl⟩—H | |

These compounds can be employed, for example, in process step (d).

In process step (d), the compounds of the general formula (I) are obtained from the compounds of the general formula (VI) and (V).

If, for example, 0-ethyl-0-isopropyl chlorothionophosphate and 5-hydroxy-2-phenyl-pyrimidine are employed as starting materials in process step (d), then the corresponding reaction can be outlined by the following equation:

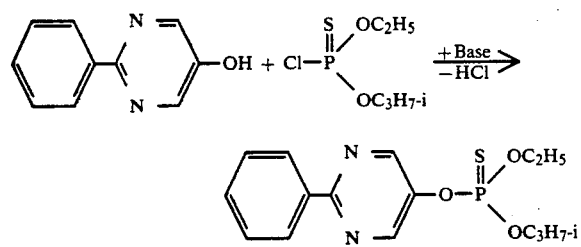

The starting materials of the general formula (VI) to be employed in process step (d) are known and can be easily prepared commercially by processes which are known from the literature. The following may be individually mentioned as examples thereof: O,O-dimethyl, O,O-diethyl, O,O-di-n-propyl, O,O-di-iso-propyl, O,O-di-n-butyl, O,O-di-iso-butyl, O,O-di-sec-butyl, O-methyl O-ethyl, O-methyl O-n-propyl, O-methyl O-iso-propyl, O-methyl O-n-butyl, O-methyl O-iso-butyl, O-methyl O-sec butyl, O-ethyl O-n-propyl, O-ethyl O-isopropyl, O-ethyl O-n-butyl, O-ethyl O-sec-butyl, O-ethyl O-iso-butyl, O-n-propyl O-butyl or O-iso-propyl O-butyl chlorophosphate and the corresponding thiono analogues, furthermore O,S-dimethyl, O,S-diethyl, O,S-di-n-propyl, O,S-di-iso-propyl, O,S-di-n-butyl, O,S-di-iso-butyl, O-ethyl S-n-propyl, O-ethyl S-iso-propyl, O-ethyl S-n-butyl, O-ethyl S-sec-butyl, O-n-propyl S-ethyl, O-n-propyl S-iso-propyl, O-n-butyl S-n-propyl and O-sec-butyl S-ethyl chlorothiophosphate and the corresponding thio analogues, furthermore O-methyl, O-ethyl, O-n-propyl, O-iso-propyl, O-n-butyl, O-iso-butyl or O-sec-butyl methane- or ethane-, n-propane-, n-butane-, iso-butane-, sec-butaneor phenylchlorophosphonate and the corresponding thiono analogues, and O-methyl N-methyl-, O-methyl N-ethyl-, O-methyl N-n-propyl-, O-methyl N-iso-propyl-, O-ethyl N-methyl-, O-ethyl N-ethyl-, O-ethyl N-n-propyl-, O-ethyl N-iso-propyl-, O-n-propyl N-methyl-, O-n-propyl N-ethyl-, O-n-propyl N-n-propyl-, O-n-propyl N-iso-propyl-, O-iso-propyl N-methyl-, O-isopropyl N-iso-propyl-, O-iso-propyl N-n-propyl-, O-iso-propyl N-iso-ethyl-, O-n-butyl N-methyl-, O-n-butyl N-ethyl-, O-n-propyl-, O-n-butyl N-n-propyl-, O-n-butyl N-iso-propyl-, O-iso-butyl N-methyl-, O-iso-butyl N-ethyl-, O-iso-butyl N-n-propyl-, O-iso-butyl N-iso-propyl-, O-sec-butyl N-methyl-, O-sec-butyl N-ethyl-, O-sec-butyl-N-n-propyl-, and O-sec-butyl N-iso-propyl-chlorophosphoramide and the corresponding thiono analogues.

The process step (d) for the preparation of the compounds of the general formula (I) is preferably carried also using suitable solvents and diluents. Those which are suitable are practically all inert organic solvents. In particular, these include aliphatic and aromatic, optionally chlorinated hydrocarbons, such as benzene, toluene, xylene, benzine, methylene chloride, chloroform, carbon tetrachloride, chlorobenzene or ethers, such as diethyl ether and dibutyl ether, dioxane, furthermore ketones, for example acetone, methyl ethyl, methyl isopropyl and methyl isobutyl ketone, and in addition nitriles, such as acetonitrile and propionitrile.

All customary acid-binding agents can be used as acid acceptors. Alkali metal carbonates and alkoxides, such as sodium carbonate and potassium carbonate, potassium tert-butoxide, furthermore aliphatic, aromatic or heterocyclic amines, for example triethylamine, trimethylamine, dimethylaniline, dimethylbenzylamine and pyridine are particularly successful.

The reaction temperature can be varied within a relatively wide range. In general, the reaction is carried out between 0° C. and 100° C., preferably at 20° C. to 60° C.

In general, the reaction is allowed to run at atmospheric pressure.

To carry out the process variant (d), the starting materials are mostly employed in equivalent proportions. An excess of one or the other components brings no substantial advantages. The reaction components are mostly combined in one of the abovementioned solvents in the presence of an acid-binding agent and stirred for one or more hours at elevated temperature to complete the reaction. An organic solvent, for example toluene, is then added to the mixture and the organic phase is worked up in the customary manner by washing, drying and distilling off the solvent.

The compounds of the general formula (I) are mostly produced in the form of oils which frequently cannot be distilled without decomposition, but which are freed from the last volatile components by so-called "incipient distillation", i.e. by relatively long heating under reduced pressure at moderately elevated temperature and are purified in this manner. The refractive index is used for their characterization.

As already mentioned several times, the compounds of the general formula (I) which can be obtained according to the invention are distinguished by outstanding insecticidal, acaricidal and nematicidal action. They are active against plants, hygiene and storage pests and in the veterinary medicine sector. They possess a good action against both sucking and biting insects and mites, combined with low phytotoxicity.

On this basis, the compounds of the general formula (I) which can be obtained according to the invention can be employed successfully in plant protection and also in the hygiene, storage protection and veterinary sector as pest combating agents.

Many of the compounds which can be obtained according to the invention and their use are known and are described, for example, in DE-OS (German Published Specification) 2,643,262, U.S. Pat. No. 4,127,652, EP-A 0,009,566, U.S. Pat. No. 4,325,948, U.S. Pat No. 4,444,764 and U.S. Pat. No. 4,429,125.

As already explained above, it is possible by the process according to the invention according to process steps (a) to (d) to prepare the valuable compounds of the general formula (I) in smooth reactions in a simple manner, excellent total yields being obtained. The process (a) to (d) according to the invention opens up a path in a surprising manner by the special combination of the process steps and by the partial introduction of new compounds obtained in this connection which permits an economical preparation of the compounds of the general formula (I) which previously could not be achieved.

Since the individual intermediates are stable and, above all, in the case of their isolation can be stored over a relatively long time, the process according to the invention moreover permits remarkable flexibility in production, so that with rapidly arising need for the final products, needs-directed production is possible, which can be of very great significance in the plant protection field, in particular because of the climatically caused seasonal variations.

The process according to the invention (or process steps) and compounds are illustrated by the preparation examples below All percentages are by weight, unless indicated otherwise.

(A) Process for the preparation of the compounds of the general formula (IV)

Process variant (a1)

Example A1

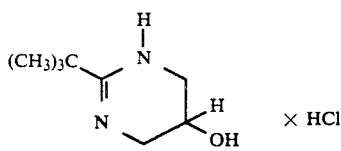

13.6 g (0.1 mol) of pivalamidine hydrochloride are added in portions to a solution of 9 g (0.1 mol) of 1,3-diamino-propan-2-ol in 30 ml of ethanol. The mixture is boiled under reflux for 90 minutes and cooled to room temperature, and 70 ml of diethyl ether are added. The precipitated product is filtered off with suction.

19 g (99% of theory) of 2-tert-butyl-5-hydroxy-3,4,5,6-tetrahydropyrimidine hydrochloride are thus obtained in the form of colorless, strongly hygroscopic crystals.

Example A2

22.8 g (0.15 mol) of pivalyliminoethyl ether hydrochloride are added in portions to a solution of 13.5 g (0.15 mol) of 1,3-diamino-propan-2-ol in 30 ml of ethanol and the mixture is boiled under reflux for 2 hours. Analogously to the work-up described under Example 1, 28.5 g (99% of theory) of 2-tert-butyl-5-hydroxy-3,4,5,6-tetrahydropyrimidine hydrochloride are obtained.

The compounds of the formula (IV) detailed below are obtained analogously to Examples A1 and A2 and under consideration of the instructions in the description for process variant (a1) according to the invention:

TABLE 6

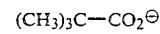

| Ex. No. | R |
|---------|---|
| A3 | —C₃H₇-n |
| A4 | H |
| A5 | —CH₃ |
| A6 | —N(CH₃)₂ |
| A7 | —C₂H₅ |
| A8 | cyclohexyl |
| A9 | phenyl |

Process variant (a2)

Example A10

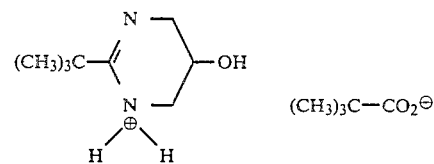

306 g (3 mols) of pivalic acid and 135 g (1.5 mols) of 1,3-diamino-propan-2-ol are boiled in a water separator for 22 hours in 3 liters of xylene mixture. After this, about 55 ml of water have separated. The mixture is allowed to cool, and the precipitate is filtered off with suction and dried. 325 g (84% of theory) of white crystals of melting point 154° C. are obtained.

The following new compounds of the formula IV are obtained analogously to Example A10:

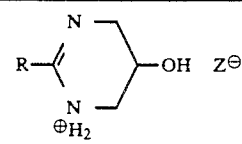

| Example | R | | Yield % of theory | Physical data |
|---------|---|---|---|---|
| A11 | (C₂H₅)₂CH— | (C₂H₅)₂CHCO₂⁻ | 77,4 | yellow oil |
| A12 | cyclopropyl | cyclopropyl-CO₂⁻ | 60,3 | red oil |
| A13 | Benzyl | Benzyl-CO₂⁻ | 91,2 | m.p. |

-continued

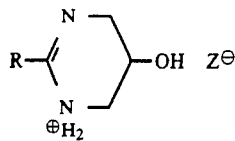

| Example | | | Yield % of theory | Physical data |
|---|---|---|---|---|
| A14 | CH₃OCH₂— | CH₃OCH₂CO₂⁻ | 78,4 | 152° C. m.p. |
| A15 | CH₃— | CH₃CO₂⁻ | 83,3 | 92° C. yellow hygroscopic crystals |

Process variant (a2)

Example A16

441 g (3 mols) of the di-pivalate salt of 1,3-di-amino-propan-2-ol

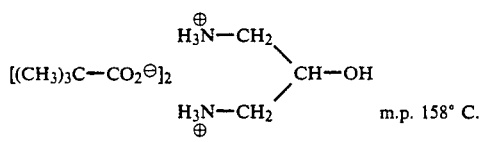

m.p. 158° C.

are boiled in a water separator for 22 hours in 3 liters of xylene mixture. Working up takes place as in Example A10.

(B) Process for the preparation of the compounds of the general formula (IVa)

Example B1

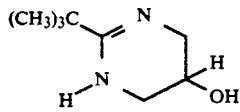

57.7 g (0.3 mol) of 2-tert-butyl-5-hydroxy-3,4,5,6-tetrahydropyrimidine hydrochloride are dissolved in 100 ml of water and 20 ml of 45 percent strength sodium hydroxide solution are added. The precipitated product is filtered off with suction. 32.7 g (70% of theory) of 2-tert-butyl-5-hydroxy-3,4,5,6-tetrahydropyrimidine are thus obtained in the form of colorless crystals having melting point 210° C.

The compounds of the formula (IVa) detailed below are obtained analogously to Example B1 and with consideration of the instructions in the description for process step (b) according to the invention:

TABLE 7

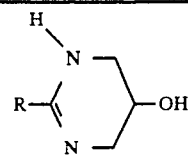

| Example No. | R |
|---|---|
| B2 | —C₃H₇-n |
| B3 | H |
| B4 | —CH₃ |
| B5 | —N(CH₃)₂ |

TABLE 7-continued (IVa)

| Example No. | R |
|---|---|
| B6 | —C₂H₅ |
| B7 |  |
| B8 |  |

Example B]

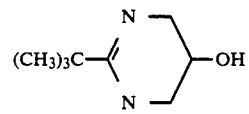

12.9 g (0.05 mol) of the pivalate salt of 5-hydroxy-2-tert.-butyl-tetrahydropyrimidine are dissolved in 60 ml of water and a strongly basic ion exchanger (Lewatit MP 500; Lewatit=trademark of BAYER AG, Leverkusen, Federal Republic of Germany) is added. The mixture is stirred for about 5 minutes, the ion exchanger is filtered off with suction and the aqueous mother liquor is concentrated in vacuo ( vapor diffusion pump) at 30° C. 7.4 g of 5-hydroxy-2-tert.-butyl-tetrahydropyrimidine (free base) remains in the form of white crystals. This corresponds to a yield of 94.9% of theory.

(C) Process for the preparation of the compounds of the general formula (V) [process step (c)]

Example C1

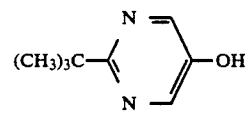

10.4 g (0.066 mol) of potassium permanganate are added dropwise in portions with cooling during the course of about 20 minutes to 15.8 g of 1,4,5,6-tetrahydro-2-tertbutyl-5-hydroxypyrimidine in 80 ml of water in such a way that the reaction temperature does not exceed 40° C. After the addition, the mixture is stirred in a water bath for one hour, then at 90° C. for 10 minutes and filtered with suction while warm. The filtrate is adjusted to pH 4–5 at room temperature using concentrated hydrochloric acid and allowed to stand for about one hour in an ice bath, and the crystalline precipitate of 5-hydroxy-2-tert-butylpyrimidine is filtered off with suction and dried in air (m.p.:132° C.).

The compounds of the formula (V) detailed below are obtained analogously to Example C1 and under consideration of the instructions in the description for process step (c) according to the invention:

TABLE 8

$$R-\underset{N}{\overset{N=}{\diagdown}}-OH \quad (V)$$

| Example No. | R | M.p. [°C.] |
|---|---|---|
| C2 | —C₃H₇-n | 117 |
| C3 | H | 216 |
| C4 | —CH₃ | 173 |
| C5 | —N(CH₃)₂ | 164 |
| C6 | —C₂H₅ | 149 |
| C7 | cyclohexyl (H) | 165 |
| C8 | phenyl | 145 |

Example C9

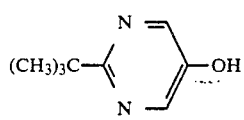

A mixture of 5.0 g (0.032 mol) of 3,4,5,6-tetrahydro-2-tert.-butyl-5-hydroxypyrimidine (99%), 11.8 g (0.10 mol) of potassium tert.-butoxide (about 95%) and 25 g of t-butanol is vigorously stirred at 60° C. in an oxygen atmosphere under atmospheric pressure. The oxygen consumption is measured by a gas burette. After 30 minutes, the oxygen uptake comes to a halt after a total uptake of 0.038 mol of oxygen.

For working up, 5 ml of water are added to the reaction mixture, the t-butanol is distilled off under reduced pressure, and the residue is taken up in 50 ml of water and acidified to pH=4.5 with 1:1 hydrochloric acid. The mixture is then extracted 3 x using diethyl ether, the organic phase is dried over sodium sulphate and the solvent is evaporated off. 1.98 g of crystalline residue containing 88.2% of 2-tert.-butyl-5-hydroxypyrimidine remain, corresponding to a yield of 35.9%.

Example C10

Procedure as Example C9 with the difference that 0.10 g of copper(II) oxide are added. After a reaction time of 20 minutes, 0.035 mol of oxygen have been taken up.

To isolate the product, the reaction mixture is hydrolyzed using 5 ml of water, the solvent is distilled off under reduced pressure and the residue is taken up in 50 ml of water. After filtering to separate off the copper oxide hydrate, the aqueous solution is acidified to pH=4.5 using 1:1 hydrochloric acid and extracted with diethyl ether, and the ether phase is dried over sodium sulphate and evaporated. 3.71 g of crystalline product remain as a residue containing 89.4% of 2-tert.-butyl-5-hydroxypyrimidine, corresponding to a yield of 68.1%.

Example C11

Procedure as in Example C9 with the difference that 0.10 g of CuO and additionally 0.10 g of MnO₂ are added as a catalyst. Work-up as in Example C10.

Crude product 4.0 g containing 91.3% of 2-tert.-butyl-5-hydroxypyrimidine, corresponding to a yield of 75.0%.

Example C12

Procedure as Example C9 with the difference that 0.10 g of cobalt(II) chloride are added. Work-up as in Example C10. Yield: 49.7%

Example C13

A mixture of 6.50 g (0.025 mol) of the salt of 3,4,5,6-tetrahydro-2-tert.-butyl-5-hydroxypyrimidine and pivalic acid, 14.5 g (0.123 mol) of potassium tert.-butoxide (0.95%), 0.08 g of copper-II-oxide and 40 g of t-butanol is vigorously stirred at 60° C. in an oxygen atmosphere under atmospheric pressure. After a reaction time of 30 minutes, the oxygen uptake is complete with a total uptake of 0.31 mol. Work-up as in Example C10.

Crude product 5.70 g containing 45.5% of 2-tert.-butyl-5-hydroxypyrimidine, corresponding to a yield of 67.7%.

Example C14

A mixture of 5.0 g (0.032 mol) of 3,4,5,6-tetrahydro-2-tert.-butyl-5-hydroxypyrimidine (99% pure), 4.0 g of sodium hydroxide (0.10 mol) 25 g of dimethyl sulphoxide and 0.10 g of copper(II) oxide is vigorously stirred at 60° C. in an oxygen atmosphere at atmospheric pressure. After 60 minutes, the oxygen uptake is complete with a total uptake of 0.039 mol.

To isolate the product, the dimethyl sulphoxide is completely evaporated in vacuo as soon as possible by the addition of heat, the solid residue is then taken up in 50 ml of water and the aqueous alkaline solution is filtered to separate off the copper oxide hydrate. The filtrate is acidified to pH=4.5 and extracted using diethyl ether, and the ether phase is dried over sodium sulphate and evaporated. 4.15 g of crystalline product containing 88.1% of 2-tert.-butyl-5-hydroxypyrimidine remain as a residue, corresponding to a yield of 75.1%.

Example C15

A mixture of 5.0 g (0.032 mol) of 3,4,5,6-tetrahydro-2-tert.-butyl-5-hydroxypyrimidine (99%), 6.6 g (0.10 mol) of potassium hydroxide (about 85%), 40 g of 0.1 g of copper oxide and 0.1 g of manganese dioxide is vigorously stirred in an oxygen atmosphere at 90° C. under atmospheric pressure. 0.038 mol of oxygen is taken up during 4 hours.

Work-up as in Example C10.

Crude product 3.05 g containing 68.3of 2-tert.-butyl-5-hydroxypyrimidine. Yield: 42.8%.

Example C16

A mixture of 5.0 g (0.032 mol) of 3,4,5,6-tetrahydro-2-tert.-butyl-5-hydroxypyrimidine (99%), 11.8 g (0.10 mol) of potassium tert.-butoxide (95%), 40 g of dimethylformamide and 0.10 g of copper(II) oxide is stirred in an oxygen atmosphere at 60° C. After 15 minutes, the oxygen uptake is complete with a total uptake of 0.036 mol.

Work-up as in Example C10. Yield: 55.9%

(D) Process for the preparation of the compounds of the general formula (I) [process variant (d)]

Example D1

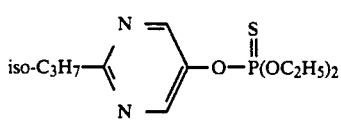

A mixture of 300 ml of acetonitrile, 13.8 g (0.1 mol) of 2-iso-propyl-5-hydroxy-pyrimidine, 20.7 g (0.15 mol) of potassium carbonate and 18.8 g (0.1 mol) of O,O-diethyl chlorothionophosphate is stirred for 2 hours at 45° C. The reaction mixture is then poured into 400 ml of toluene and washed twice with 300 ml each of water. The toluene solution is dried over sodium sulphate and evaporated in vacuo. The residue is distilled in high vacuum.

17.4 g (62% of theory) of O,O-diethyl-[2-iso-propyl-pyrimidin-5-yl]-thionophosphate are thus obtained in the form of a brown oil having refractive index $n_D^{21} = 1.4970$.

The following compounds of the formula (I)

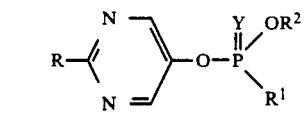

can be prepared in an analogous manner:

TABLE 9

| Example No. | R | $OR^2$ | $R^1$ | Y | Yield (% of theory) | Refractive index |
|---|---|---|---|---|---|---|
| D2 | $C_3H_7$-i | $CH_3$ | $C_3H_7$-i | S | 74 | $n_D^{21}$: 1.5102 |
| D3 | $CH_3$ | $OCH_3$ | $C_3H_7$-i | S | 66 | $n_D^{24}$: 1.5080 |
| D4 | $C_2H_5$ | $SC_3H_7$-n | $C_3H_7$-i | S | 69 | $n_D^{26}$: 1.5284 |
| D5 | $C_2H_5$ | ⌬ | $C_3H_7$-i | S | 74 | $n_D^{26}$: 1.5570 |
| D6 | $C_2H_5$ | $OC_2H_5$ | $C_3H_7$-i | O | 82 | $n_D^{32}$: 1.4630 |
| D7 | $C_2H_5$ | $NH-C_3H_7$-i | $C_3H_7$-i | S | 57 | $n_D^{32}$: 1.5057 |
| D8 | $C_3H_7$-n | $OC_2H_5$ | $C_3H_7$-i | S | 73 | $n_D^{32}$: 1.4929 |
| D9 | $C_2H_5$ | $OC_2H_5$ | $CH_3$ | S | 92 | $n_D^{32}$: 1.4992 |
| D10 | $C_2H_5$ | $C_2H_5$ | $CH_3$ | S | 80 | $n_D^{32}$: 1.5169 |
| D11 | $C_2H_5$ | $OC_2H_5$ | ⌬ | S | 80 | $n_D^{32}$: 1.5643 |
| D12 | $C_2H_5$ | $C_2H_5$ | ⌬ | S | 80 | $n_D^{32}$: 1.5827 |
| D13 | $C_2H_5$ | $OC_2H_5$ | H | S | 72 | $n_D^{32}$: 1.5028 |
| D14 | $C_2H_5$ | $OC_2H_5$ | $-C_2H_5$ | S | 84 | $n_D^{20}$: 1.5014 |
| D15 | $C_2H_5$ | $OC_2H_5$ | $-C_3H_7$-n | S | 60 | $n_D^{26}$: 1.4833 |
| D16 | $C_2H_5$ | $OC_2H_5$ | $-C_4H_9$-n | S | 94 | $n_D^{21}$: 1.4958 |
| D17 | $C_2H_5$ | $OC_2H_5$ | $-C_4H_9$-t | S | 61 | $n_D^{26}$: 1.4902 |
| D18 | $C_2H_5$ | $OC_2H_5$ | cyclohexyl-H | S | 66 | $n_D^{23}$: 1.5158 |
| D19 | $C_2H_5$ | $-NHOC_3H_7$-i | cyclohexyl-H | S | 51 | $n_D^{23}$: 1.5246 |
| D20 | $CH_3$ | $-OCH_3$ | cyclohexyl-H | S | 64 | $n_D^{23}$: 1.5287 |
| D21 | $C_2H_5$ | $OC_2H_5$ | cyclopropyl | S | 78 | $n_D^{24}$: 1.5142 |
| D22 | $C_2H_5$ | $NHC_3H_7$-i | cyclopropyl | S | 62 | 49° C. (mp) |

TABLE 9-continued
| Example No. | | | | | Yield (% of theory) | Refractive index |
|---|---|---|---|---|---|---|
| D23 | $CH_3$ | $OCH_3$ | 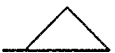 | S | 43 | $n_D^{24}$: 1.5390 |
| D24 | $C_3H_7$-n | $OC_2H_5$ |  | S | 71 | $n_D^{25}$: 1.5128 |
| D25 | $C_2H_5$ | $NHC_2H_5$ |  | S | 74 | $n_D^{26}$: 1.5310 |
| D26 | $C_2H_5$ | $OC_2H_5$ |  | S | | |
| D27 | $C_2H_5$ | $OC_2H_5$ |  | S | | |
| D28 | $C_2H_5$ | $OC_2H_5$ | 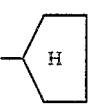 | S | 80 | $n_D^{23}$: 1.5164 |
| D29 | $C_2H_5$ | $OC_3H_7$-n | 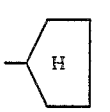 | | | |
| D30 | $C_2H_5$ | $CH_3$ | 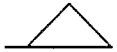 | S | 72 | $n_D^{25}$: 1.5428 |
| D31 | $C_2H_5$ | $OC_2H_5$ |  | O | | |
| D32 | $C_2H_5$ | $NHC_3H_7$-i | 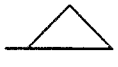 | O | | |
| D33 | $C_2H_5$ |  |  | S | 74 | $n_D^{25}$: 1.5815 |
| D34 | $C_2H_5$ | $SC_3H_7$-n | 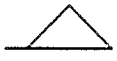 | S | | |
| D35 | $C_2H_5$ |  | H | S | | |
| D36 | $C_2H_5$ | $NHC_2H_5$ | H | S | 66 | $n_D^{23}$: 1.5329 |
| D37 | $C_2H_5$ | $SC_3H_7$ | 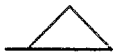 | O | | |
| D38 | $C_2H_5$ | $C_2H_5$ | 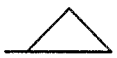 | S | | |
| D39 | $CH_3$ | $C_2H_5$ |  | S | | |
| D40 | $C_3H_7$-i | $CH_3$ |  | S | 67 | $n_D^{26}$: 1.5233 |

TABLE 9-continued

| Example No. | | | | Yield (% of theory) | Refractive index |
|---|---|---|---|---|---|
| D41 | $CH_3$ | $NHC_3H_7$-i | △△ | S | |
| D42 | $CH_3$ | $NHCH_3$ | △△ | S | 66 | $n_D^{26}$: 1.5460 |
| D43 | $C_2H_5$ | $NHCH_3$ | △ | S | |
| D44 | $CH_3$ | $NHC_2H_5$ | △ | S | |
| D45 | $C_2H_5$ | $NH-C_3H_7$-i | (pentyl-H) | S | 55 | $n_D^{23}$: 1.5247 |
| D46 | $C_2H_5$ | $OC_2H_5$ | $H_3C$-△ | S | |
| D47 | $C_2H_5$ | $OC_3H_7$-i | $-C_3H_7$-i | S | 92 | $n_D^{23}$: 1.4910 |
| D48 | $C_3H_7$-i | $C_3H_7$-i | $-OC_3H_7$-i | S | | $n_D^{20}$: 1.4869 |
| D49 | $C_4H_9$-t | $C_2H_5$ | $-OC_3H_7$-i | S | | $n_D^{20}$: 1.4917 |
| D50 | $C_3H_7$-i | $C_2H_5$ | $-OC_4H_9$-s | S | | $n_D^{20}$: 1.4960 |
| D51 | $C_4H_9$-t | $C_2H_5$ | $-OC_4H_9$-s | S | | $n_D^{22}$: 1.4935 |
| D52 | $C_4H_9$-t | $C_3H_7$-i | $-OC_3H_7$-i | S | | $n_D^{22}$: 1.4857 |
| D53 | phenyl | $C_2H_5$ | $-OC_3H_7$-i | S | | $n_D^{22}$: 1.5516 |
| D54 | $C_4H_9$-t | $C_2H_5$ | $-NHC_2H_5$ | S | | $n_D^{21}$: 1.5100 |
| D55 | phenyl | $C_2H_5$ | $-OC_4H_9$-s | S | |
| D56 | phenyl | $C_3H_7$-i | $-OC_3H_7$-i | S | |
| D57 | $C_3H_7$-i | $C_3H_7$-n | $-OC_3H_7$-n | S | | $n_D^{23}$: 1.4915 |

It will be appreciated that the instant specification and claims are set forth by way of illustration and not limitation, and that various modifications and changes may be made without departing from the spirit and scope of the present invention.

What is claimed is:

1. A process for the preparation of a compound of the formula

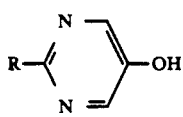

(V)

in which:

R represents hydrogen, alkoxy having 1 to 12 carbon atoms, alkylamino of dialkylamino each having 1 to 6 carbon atoms in each alkyl group, alkyl having 1 to 12 carbon atoms which is unsubstituted or substituted by alkoxy having 1 to 4 carbon atoms or alkylsulphonyl having 1 to 4 carbon atoms in the alkyl group, cycloalkyl having 3 to 8 carbon atoms which is unsubstituted or substituted by alkyl having 1 to 4 carbon atoms, or aryl having 6 to 10 carbon atoms or benzyl which are each unsubstituted or substituted by alkyl, alkoxy or alkylsulphonyl each having 1 to 4 carbon atoms in the alkyl group;

comprising oxidizing a 5-hydroxy-3,4,5,6-tetrahydropyrimidine salt of the formula

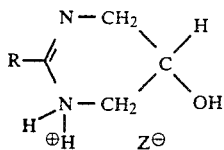

in which

Z is chlorine or $R^5$—$CO_2$, and $R^5$ represents alkoxy, alkylthio, alkylamino or dialkylamino each having 1 to 6 carbon atoms in the aklyl group, or phenyl each being unsubstituted or substituted by one or more substituents independently selected from the group consisting of alkyl, alkoxy, and alkylthio each having 1 to 4 carbon atoms, halogen, cyano, and nitro;

or the corresponding free 5-hydroxy-3,4,5,6-tetrahydropyrimidine of the formula

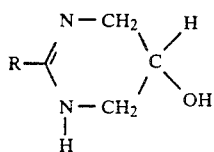

in the liquid phase in the presence of a solvent and a base at a temperature between about 0° C. and 300° C. using oxygen or an oxygen-containing gas.

2. A process according to claim 1, in which

R is hydrogen, alkoxy having 1 to 6 carbon atoms, mono- or dialkylamino having 1 to 4 carbon atoms in each alkyl moiety, alkyl having 1 to 6 carbon atoms and optionally substituted by methoxy, ethoxy, methylsulphonyl or ethylsulphonyl, cycloalkyl having 3 to 6 carbon atoms and optionally substituted by methyl or ethyl, or phenyl which is optionally substituted by methyl, ethyl, methoxy, ethoxy, methylsulphonyl or ethyl-sulphonyl.

3. A process according to claim 1, in which

R is methyl, isopropyl or tert.-butyl.

4. A process, according to claim 1, in which $R^1$ is ethoxy, $R^2$ is ethyl or s-butyl, and Y is sulphur.

5. A process according to claim 1, wherein the oxidation is effected in the presence of a transition metal compound as catalyst.

6. A process for the preparation of a compound of the formula

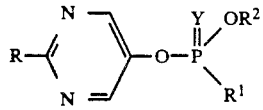

in which

R represents hydrogen, alkoxy having 1 to 12 carbon atoms, alkylamino or dialkylamino each having 1 to 6 carbon atoms in each alkyl group, alkyl having 1 to 12 carbon atoms which is unsubstituted or substituted by alkoxy having 1 to 4 carbon atoms or alkylsulphonyl having 1 to 4 carbon atoms in the alkyl group, cycloalkyl having 3 to 8 carbon atoms which is unsubstituted or substituted by alkyl having 1 to 4 carbon atoms, or aryl having 6 to 10 carbon atoms or benzyl which are each unsubstituted or substituted by alkyl, alkoxy or alkylsulphonyl each having 1 to 4 carbon atoms in the alkyl group;

$R^1$ represents alkoxy, alkylthio, alkylamino or dialkylamino each having 1 to 6 carbon atoms in the alkyl group, or phenyl each being unsubstituted or substituted by one or more substituents independently selected from the group consisting of alkyl, alkoxy, and alkylthio each having 1 to 4 carbon atoms, halogen, cyano, and nitro; or represents alkyl having 1 to 6 carbon atoms which is unsubstituted or substituted by one or more substituents independently selected from the group consisting of alkoxy and alkylthio each having 1 to 4 carbon atoms, halogen, cyano, and nitro;

$R^2$ represents alkyl having 1 to 6 carbon atoms which is unsubstituted or substituted by one or more substituents independently selected from the group consisting of alkoxy and alkylthio each having 1 to 4 carbon atoms, halogen, cyano, and nitro; and Y represents oxygen or sulfur;

comprising (a1) reacting a compound of the formula

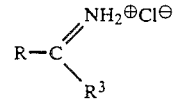

in which $R^3$ represents amino, with 1,3-diamino-2-propanol of the formula

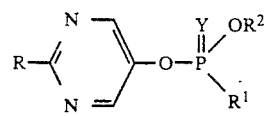

or an acid addition salt thereof, optionally in the presence or absence of a diluent, at a temperature between about 0° C. and 120° C.;

(a2) reacting a carboxylic acid of the formula

in which $R^5$ represents alkoxy, alkylthio, alkylamino or dialkylamino each having 1 to 6 carbon atoms in the alkyl group, or phenyl each being unsubstituted or substituted by one or more substituents independently selected from the group consisting of alkyl, alkoxy, and alkylthio each having 1 to 4 carbon atoms, halogen, cyano, and nitro; or represents alkyl having 1 to 6 carbon atoms which is unsubstituted or substituted by one or more substituents independently selected from the group consisting of alkoxy and alkylthio each having 1 to 4 carbon atoms, halogen, cyano, and nitro;

with 1,3-diamino-2-propanol of the formula

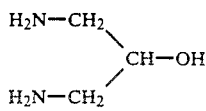

optionally in the presence of a diluent, at a temperature between 120° C. and 250° C., in a molar ratio of carboxylic acid to 1,3-diamino-2-propanol of about 1.5:1 to about 3:1; or (a3) heating a carboxylic acid salt of 1,3-diamino-2-propanol of the formula

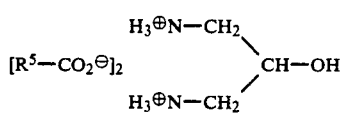 (IIc)

at a temperature between 120° C. and 250° C., to form a 5-hydroxy-3,4,5,6-tetrahydropyrimidine salt of the formula

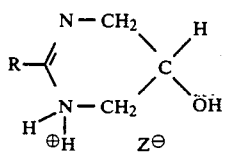 (IV)

in which

Z represents chlorine or $R^5$—$CO_2$, optionally adding base thereby to (b) produce the 5-hydroxy-3,4,5,6-tetrahydropyrimidine of the

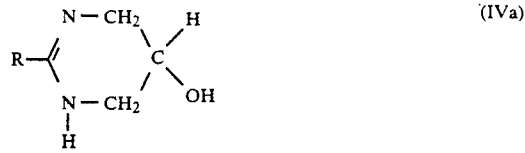 (IVa)

and subsequently (c) oxidizing the 5-hydroxy-3,4,5,6-tetrahydropyrimidine of the formula (IVa) or its salt of the formula

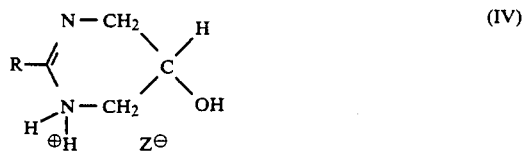 (IV)

in the liquid phase in the presence of a solvent and a base at a temperature between about 0° C. and 300° C. using oxygen or an oxygen-containing gas to give a compound of the formula

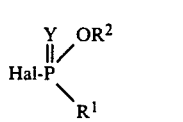 (V)

and subsequently (d) reacting the compound of the formula (V) with a compound of the formula

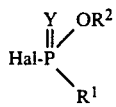 (VI)

in which
Hal represents halogen.

* * * * *

UNITED STATES PATENT AND TRADEMARK OFFICE
CERTIFICATE OF CORRECTION

PATENT NO. : 5,010,193

DATED : April 23, 1991

INVENTOR(S) : Maurer et al.

It is certified that error appears in the above-identified patent and that said Letters Patent is hereby corrected as shown below:

Col. 32, lines 35-40    Delete " 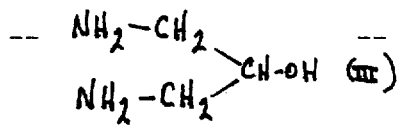 " and substitute

Col. 32, line 43    After " 120°C.; " insert -- or --

Signed and Sealed this

Twentieth Day of April, 1993

*Attest:*

MICHAEL K. KIRK

*Attesting Officer*    *Acting Commissioner of Patents and Trademarks*